United States Patent [19]

Schwarz et al.

[11] 4,414,976
[45] Nov. 15, 1983

[54] TISSUE ADHESIVE

[75] Inventors: Otto Schwarz; Yendra Linnau; Franz Löblich; Thomas Seelich, all of Vienna, Austria

[73] Assignee: Immuno Aktiengesellschaft fur chemischmedizinische Produkte, Vienna, Austria

[21] Appl. No.: 417,538

[22] Filed: Sep. 13, 1982

Related U.S. Application Data

[62] Division of Ser. No. 118,529, Feb. 4, 1980, Pat. No. 4,362,567.

[30] Foreign Application Priority Data

Feb. 15, 1979 [AT] Austria .................................. 1189/79

[51] Int. Cl.³ ............................................. A61B 17/04
[52] U.S. Cl. ................................ 128/334 R; 106/161; 106/157; 106/124; 260/112 B; 424/101; 424/177
[58] Field of Search ............................. 424/101, 177; 260/112 B; 106/161; 128/334 R

[56] References Cited

U.S. PATENT DOCUMENTS 3,523,807  8/1970  Gerendas .......................... 106/124
3,649,347  3/1972  Battista ............................... 106/161
4,362,567 12/1982  Schwarz et al. .................... 424/101

FOREIGN PATENT DOCUMENTS 448302  5/1948  Canada .

OTHER PUBLICATIONS

Chem. Abst. 84:8874t, Spaengler, 1974.
Matras, V. H. et al., *Weiner Medizinische Wochenschrift*, "Zur nahtlosen interfaszikulären Nerventransplantation im Tierexperiment" No. 37/1972 pp. 517–523.
Spangler, H. P., Wiener klinische Wochenschrift 85 (50), 827–829 1973 pp. 1–7.

*Primary Examiner*—Theodore Morris
*Attorney, Agent, or Firm*—Brumbaugh, Graves, Donohue & Raymond

[57] ABSTRACT

A tissue adhesive on the basis of human or animal protein contains factor XIII and at least 33% by weight of fibrinogen, has a ratio of factor XIII to fibrinogen, expressed in units of factor XIII per gram of fibrinogen, of at least 80, contains fibrinogen and albumin in the total protein at a ratio of 33 to 90:5 to 40, contains plasminogen-activator-inhibitor or plasmin inhibitor in an amount of 250 to 25,000 KIU per g of fibrinogen and has been lyophilized.

3 Claims, No Drawings

TISSUE ADHESIVE

This is a division of application Ser. No. 118,529, filed Feb. 4, 1980, now U.S. Pat. No. 4,362,567.

The invention relates to a tissue adhesive on the basis of human or animal proteins, containing fibrinogen and factor XIII.

It has been known for long to use blood coagulating substances for stopping bleedings and for sealing wounds. According to the first proposals of this kind, fibrin tampons and fibrin platelets, respectively, were used. During the Second World War, tissue adherences by means of blood plasma were suggested.

In recent times, a tissue adhesive on the basis of fibrinogen and factor XIII for seamless interfascicular nerve transplantations in animal experiments has been described by H. Matras et al. in "Wiener Medizinischen Wochenschrift", 1972, page 517.

A further study was carried out by Spängler et al. in "Wiener Klinischen Wochenschrift", 1973, pages 1 to 7. Also there, the possibility was shown in animal experiments of carrying out a tissue adherence with the aid of fibrinogen as a cryoprecipitate and thrombin.

The known preparations have not yet proved satisfactory, since they do not sufficiently meet the demands set to a tissue adhesive, i.e.

(a) high straining capacity of the adherences and wound sealings as well as safe and permanent blood stopping, i.e. good adhering capacity of the adhesive to the wound and tissue surfaces, as well as high internal strength of the same, (b) controllable durability of the adherences in the body, (c) complete absorbability of the adhesive in the course of the wound healing process, (d) would healing stimulating properties. This may partly be due to the fact that, in the known preparations, the coagulation factors necessary for blood stopping have not been present in an optimal proportion to one another, and also to the fact that the fibrinolytic activity in the area of adherence has not been sufficiently under control. Premature dissolutions of the tissue adherences frequently occurred due to enzymatic influence.

The invention aims at avoiding these disadvantages and difficulties and has as its object to provide a lyophilized tissue adhesive of human or animal origin, which meets the demands set out further above and which is present in a lyophilized form, which is desired for its longer durability and better transporting and storing properties.

Accordingly, the invention consists in a combination of the following characteristic features:

(a) that it contains at least 33% by weight of fibrinogen, (b) that the ratio of factor XIII to fibrinogen, expressed in units of factor XIII per gram of fibrinogen, amounts to at least 80, (c) that in the total protein, fibrinogen and albumin are contained at a ratio of 33 to 90:5 to 40, (d) that it has a content of plasminogen-activator-inhibitor or plasmin-inhibitor, preferably aprotinin, in an amount of 250 to 25,000 Kallikrein-inactivator-units (KIU) per gram of fibrinogen, (e) that the preparation has been lyophilized.

According to a preferred embodiment, the tissue adhesive additionally contains glycine, whereby the resolubility of the lyophilized product is improved.

Furthermore, the tissue adhesive additionally may contain glucose or sucrose, which components also improve the solubility.

The tissue adhesive furthermore may contain 0.2 to 200 International Units (IU) of heparin per gram of fibrinogen, whereby a stabilizing effect is obtained.

The tissue adhesive according to the invention possesses characteristic cross-linking properties after the dissolution, which are determinable by the sodiumdodecyl-sulphate-(SDS)-polyacrylamide-gel-electrophoresis method. The test is carried out in that, after mixing of the tissue adhesive with an equal volume of a solution containing 40 $\mu$Moles of $CaCl_2$ and 15 NIH-units (U.S. National Institute of Health units) of thrombin per ml, the mixture is incubated at 37° C. The cross-linking degree is determined by gel electrophoresis after stopping of the reaction and reductive splitting of the disulphide bridges contained in the proteins by the addition of a mixture of urea, sodium dodecyl sulphate and $\beta$-mercaptoethanol. Typical of the tissue adhesive according to the invention is a complete cross-linking of the fibrin-$\gamma$-chains after 3 to 5 minutes, and a cross-linking of at least 35% of the fibrin-$\alpha$-chains after two hours.

Fibrinogen, albumin and cold-insoluble globulin, in the total protein, are to be present in the tissue adhesive according to the invention at a certain ratio; this ratio amounts to 33 to 90:5 to 40:0.2 to 15.

The invention moreover comprises a method of producing the tissue adhesive described by starting out from a plasma cryoprecipitate, which method is characterized in that cold-soluble plasma-protein is removed from the cryoprecipitate by a single or repeated treatment with a buffer solution containing sodium citrate, sodium chloride, glycine, glucose and a plasminogen-activator-inhibitor or plasmin-inhibitor and heparin, the purified precipitate is dissolved, human albumin is added and the solution is lyophilized.

Advantageously, the cryoprecipitate has been produced of human or animal fresh plasma frozen at −20° C. When increasing the temperature to 0° to 2° C., the cryoprecipitate is gained and separated by centrifugation. The precipitate is eluted by a single or repeated elution with the buffer solution having a pH of 6 to 8.0, and centrifuged at 0° to 4° C. in order to remove the plasma-protein that is soluble in the cold. The treatment with the buffer solution is carried out until the desired factor-XIII-fibrinogen ratio is reached.

The purified precipitate is dissolved with a further buffer solution containing human albumin, glycine and, if desired, glucose or sucrose, a plasminogen-activator-inhibitor or plasmin inhibitor as well as heparin, and having a pH of 6.5 to 9.0, and is diluted to a protein concentration of 4.0 to 9.0%. The solution is filtered through a membrane filter having a pore size of down to 0.2 $\mu$m, filled into final containers and lyophilized.

The lyophilized tissue adhesive thus obtained can be stored at room temperature or preferably at +4° C.; it is ready for use after reconstitution with aqua ad iniectabilia, to which, if desired, a plasminogen-activator-inhibitor or a plasmin inhibitor, preferably aprotinin, can be added. When dissolving the lyophilized preparation, attention has to be paid that the solution ready for use contains at least 70 mg of fibrinogen per ml.

The tissue adhesive according to the invention can be applied universally. It can be used for seamless connection of human or animal tissue or organ parts, for sealing wounds and stopping bleedings as well as for stimulating wound healings.

Preferred fields of application in which the tissue adhesive can be successfully used are: indications in the field of ear, nose and throat surgery, oral surgery, dentistry, neurosurgery, plastic surgery, general surgery, abdonimal surgery, thorax and vascular surgery, orthopaedics, accident surgery, urology, ophthalmology and gynaecology.

Advantageously, a mixture of thrombin and calcium chloride is added to the adhesive prior to the application of the tissue adhesive according to the invention, or is applied onto the tissues to be connected.

The method of the invention is explained in more detail by way of the following example:

21 l of human plasma, which had been frozen at $-20°$ C., were heated to $+2°$ C. The resulting cryoprecipitate (435 g) was separated by centrifugation at $+2°$ C. and treated at $+2°$ C. with 4.3 l of a buffer solution adjusted at a pH of 6.5 and containing 6.6 g of $Na_3$-citrate.$2H_2O$, 3.4 g of NaCl, 10.0 g of glycine, 13.0 g of glucose.$1H_2O$, 50,000 KIU of aprotinin and 200 IU of heparin per l, and again centrifuged at $+2°$ C. The separated precipitate was dissolved in a further buffer solution having a pH of 7.9 and containing 35.0 g of human albumin, 20.0 g of glycine, 50,000 KIU of aprotinin and 200 IU of heparin per l, and diluted to a concentration of 70 mg of protein per ml.

Then the solution was sterilized by filtration through membrane filters having a pore size of down to 0.2 $\mu$m, filled into final containers at 2.2 ml each, deep-frozen and lyophilized. After reconstitution of the lyophilized product to a fibrinogen concentration of 90 mg/ml, the tissue adhesive preparation ready for use showed, in the cross-linking test, complete fibrin-$\gamma$-cross-linking after 5 minutes and 66% fibrin-$\alpha$-cross-linking after 2 hours at 37° C.

The ratio of the proteins fibrinogen to albumin to cold-insoluble globulin, contained in the tissue adhesive, was determined to be 64.0:22.3:7.7. The heparin content was 4.5 IU per g of fibrinogen. Aprotinin was contained at a concentration of 1,113 KIU per g of fibrinogen. The content of factor XIII amounted to 161 units per g of fibrinogen. The total protein content in the lyophilized preparation was 72.2%, the content of fibrinogen in the lyophilized preparation was 46.2%.

The determinations were carried out in the following manner: The determination of the factor-XIII-units was performed by means of a cross-linking test, in which factor-XIII-free fibrinogen was used as a substrate and the fibrin cross-linking caused by the addition of the unknown diluted sample served as a measure for the amount of factor XIII contained therein. A corresponding calibration curve was obtained with pooled human citrate plasma, 1 ml plasma containing 1 unit of factor XIII per definitionem. The quantitative protein determinations were carried out by the method according to Kjeldahl.

The determination of the proteins relative to one another was also performed by the SDS-polyacrylamide-gel-electrophoresis method, i.e. (a) with a non-reduced sample of the tissue adhesive and (b) with a sample reduced with $\beta$-mercaptoethanol.

What we claim is:

1. A method of seamlessly connecting tissue or organ parts, for sealing wounds, stopping bleeding and stimulating wound healing in mammals which comprises reconstituting lyophilized tissue adhesive of mammalian protein origin which comprises fibrinogen, albumin, factor XIII, cold-insoluble globulin and plasminogen-activator inhibitor or plasmin inhibitor wherein the fibrinogen is present in at least 33% by weight, in the lyophilized state; the ratio of factor XIII to fibrinogen, expressed in units of factor XIII per gram of fibrinogen is at least 80, and fibrinogen and albumin are present in a ratio of 33 to 90:5 to 40 and applying said reconstituted tissue adhesive containing at least 70 mg of fibrinogen per ml to the organ tissue or wound of a mammal in an amount sufficient to function as an adhesive.

2. A method as set forth in claim 1, wherein the tissue adhesive and a mixture of thrombin and calcium chloride are applied onto the tissue.

3. A method as set forth in claim 1, wherein, prior to applying the tissue adhesive onto the tissue to be connected, a mixture of thrombin and calcium chloride is added to the adhesive.

* * * * *